US008845722B2

(12) United States Patent  
Gabbay

(10) Patent No.: US 8,845,722 B2  
(45) Date of Patent: Sep. 30, 2014

(54) HEART VALVE PROSTHESIS AND METHOD OF IMPLANTATION THEREOF

(76) Inventor: Shlomo Gabbay, Boca Raton, FL (US)

( * ) Notice: Subject to any disclaimer, the term of this patent is extended or adjusted under 35 U.S.C. 154(b) by 172 days.

(21) Appl. No.: 12/462,352

(22) Filed: Aug. 3, 2009

(65) Prior Publication Data

US 2011/0029072 A1   Feb. 3, 2011

(51) Int. Cl.
*A61F 2/24* (2006.01)
*A61F 2/06* (2013.01)

(52) U.S. Cl.
CPC ............. *A61F 2/2409* (2013.01); *A61F 2/2418* (2013.01); *A61F 2250/0063* (2013.01)
USPC ........ 623/2.18; 623/2.13; 623/2.14; 623/2.17; 623/1.24; 623/1.26

(58) Field of Classification Search
CPC ....... A61F 2/24; A61F 2/2409; A61F 2/2412; A61F 2/2418; A61F 2/852; A61F 2002/24; A61F 2002/826
USPC ........ 623/2.1–2.4, 2.2–2.23, 2.33, 2.38, 1.24, 623/1.26
See application file for complete search history.

(56) References Cited

U.S. PATENT DOCUMENTS

| 2001/0010017 | A1* | 7/2001 | Letac et al. | 623/2.11 |
| 2001/0039450 | A1* | 11/2001 | Pavcnik et al. | 623/1.24 |
| 2002/0032481 | A1 | 3/2002 | Gabbay | |
| 2004/0210305 | A1* | 10/2004 | Shu et al. | 623/2.11 |
| 2006/0212110 | A1* | 9/2006 | Osborne et al. | 623/1.24 |
| 2006/0271166 | A1 | 11/2006 | Thill et al. | |
| 2007/0043435 | A1* | 2/2007 | Seguin et al. | 623/2.11 |
| 2008/0208327 | A1* | 8/2008 | Rowe | 623/2.11 |
| 2009/0054968 | A1* | 2/2009 | Bonhoeffer et al. | 623/1.24 |
| 2010/0036479 | A1* | 2/2010 | Hill et al. | 623/1.15 |
| 2010/0094411 | A1* | 4/2010 | Tuval et al. | 623/2.1 |

FOREIGN PATENT DOCUMENTS

| EP | 2248 486 A2 | 11/2010 |
| WO | WO 2007/013999 A2 | 2/2007 |
| WO | WO 2009/053497 A1 | 4/2009 |
| WO | WO 2009/132187 A1 | 10/2009 |
| WO | WO 2010/127041 A1 | 11/2010 |

OTHER PUBLICATIONS

European Search Report—6 pgs., Jul. 25, 2011, Shlomo Gabay.

* cited by examiner

*Primary Examiner* — Andrew Iwamaye
*Assistant Examiner* — Leslie Coburn
(74) *Attorney, Agent, or Firm* — Tarolli, Sundheim, Covell & Tummino LLP

(57) ABSTRACT

A heart valve prosthesis has a supported valve including a biological valve portion mounted within a support structure. The supported valve has inflow and outflow ends spaced axially apart from each other. A fixation support member includes an inflow portion that extends from a radially inner contact surface of the fixation support member radially outwardly and axially in a direction of the inflow end of the supported valve. An outflow portion of the fixation support member extends from the radially inner contact surface radially outwardly and axially in a direction away from the inflow portion of the fixation support member. The radially inner contact surface is attached to a radially outer surface of the supported valve adjacent the inflow end of the supported valve.

19 Claims, 9 Drawing Sheets

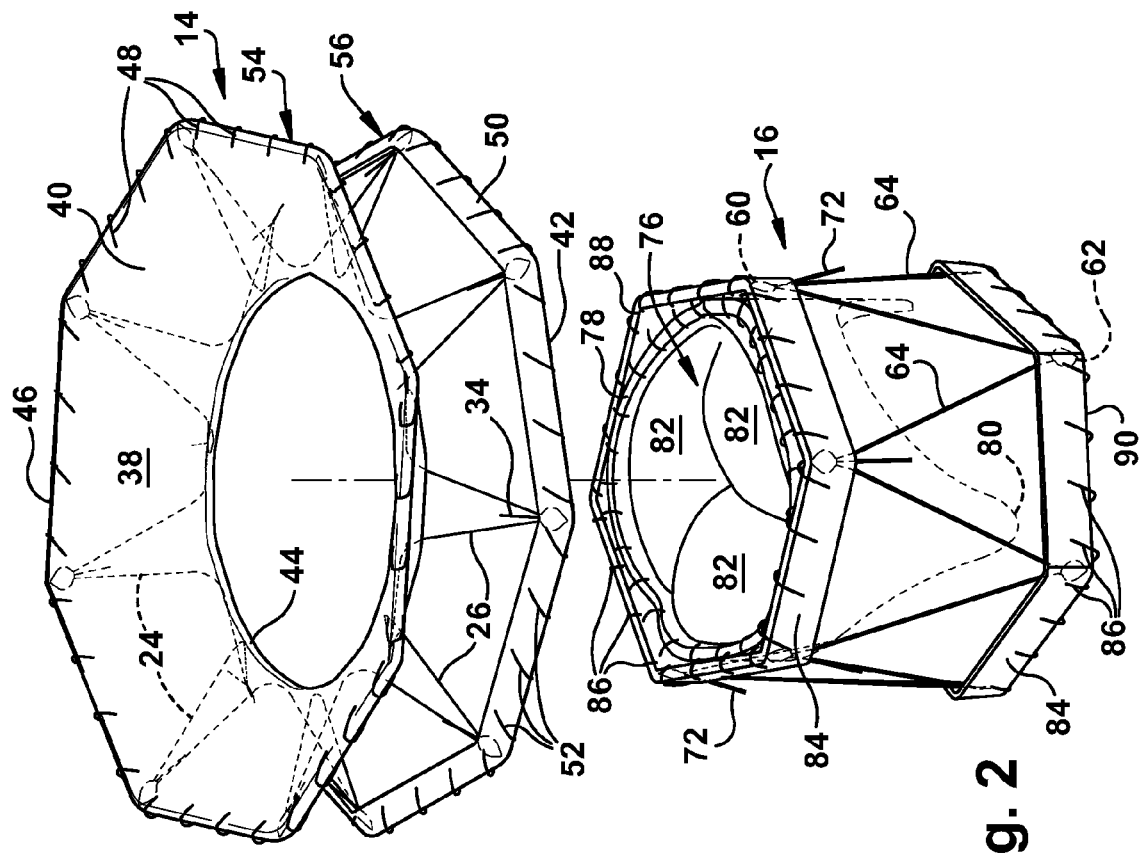
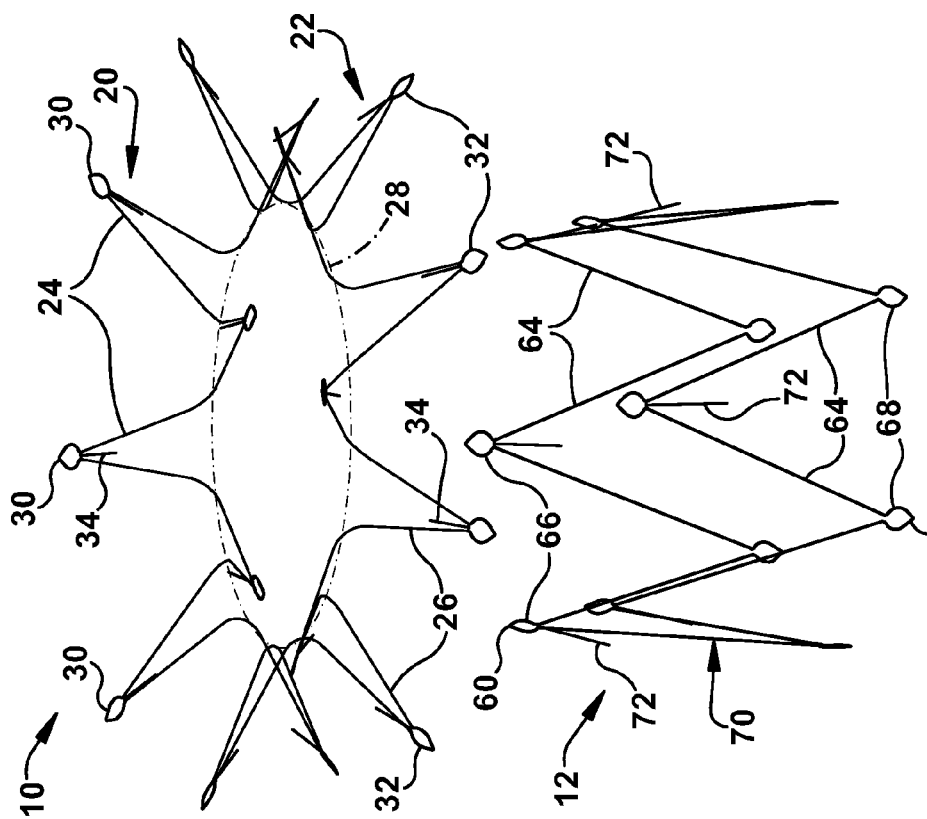
Fig. 2
Fig. 1

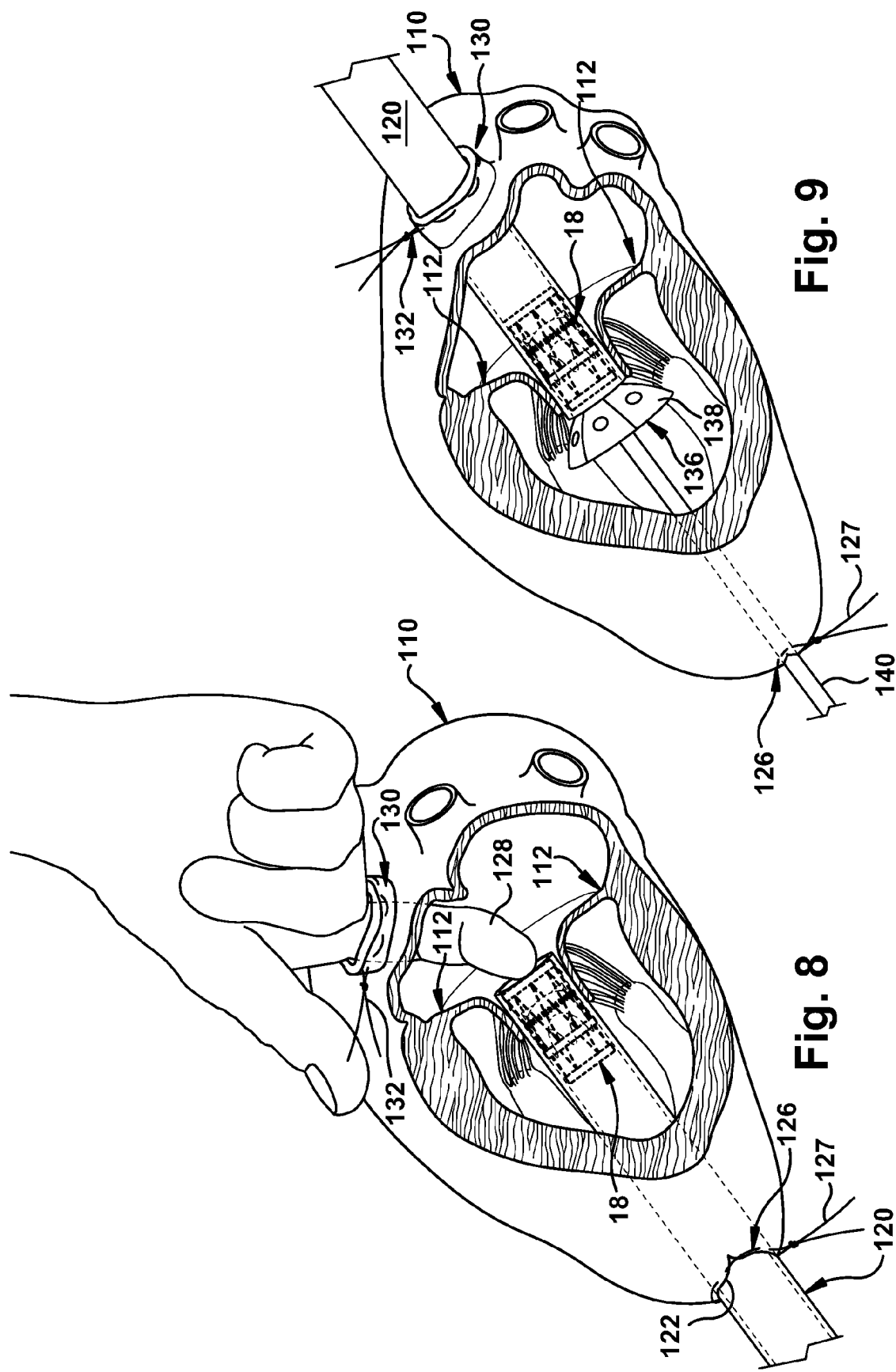

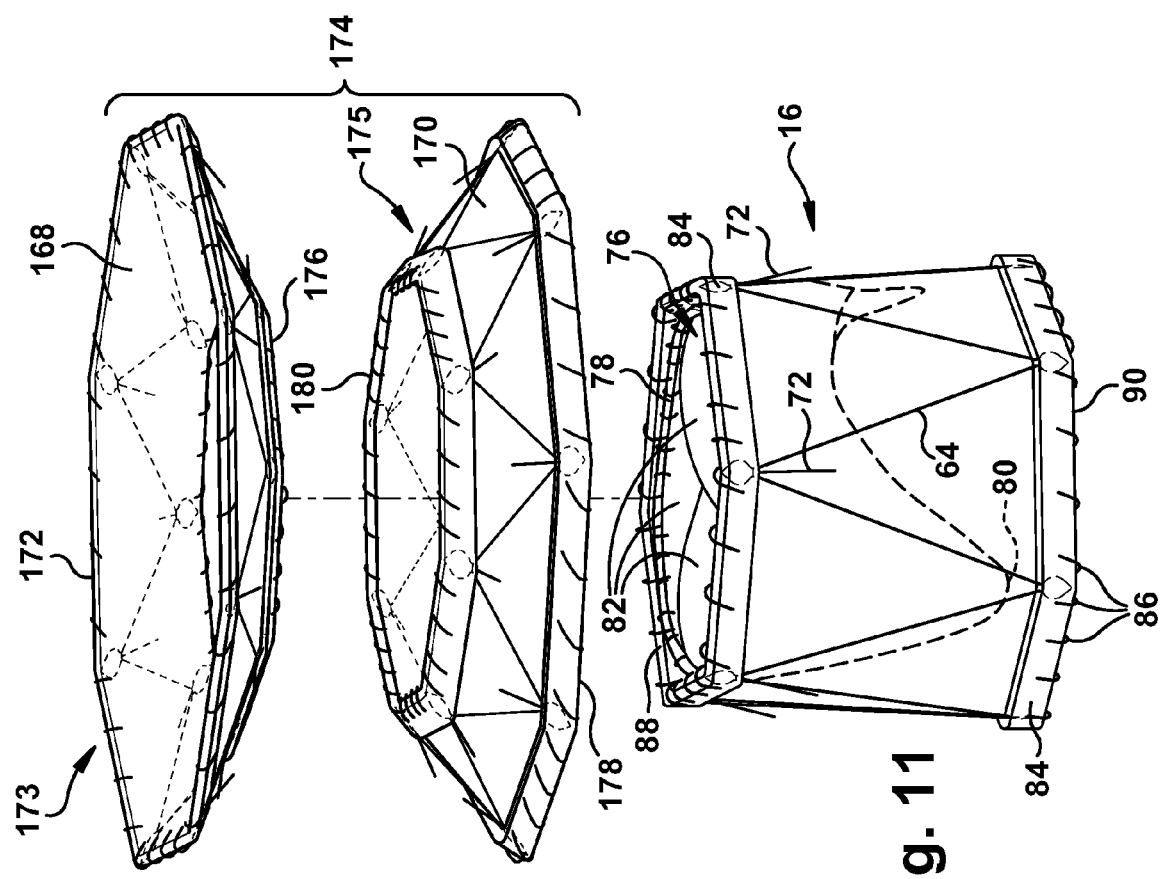
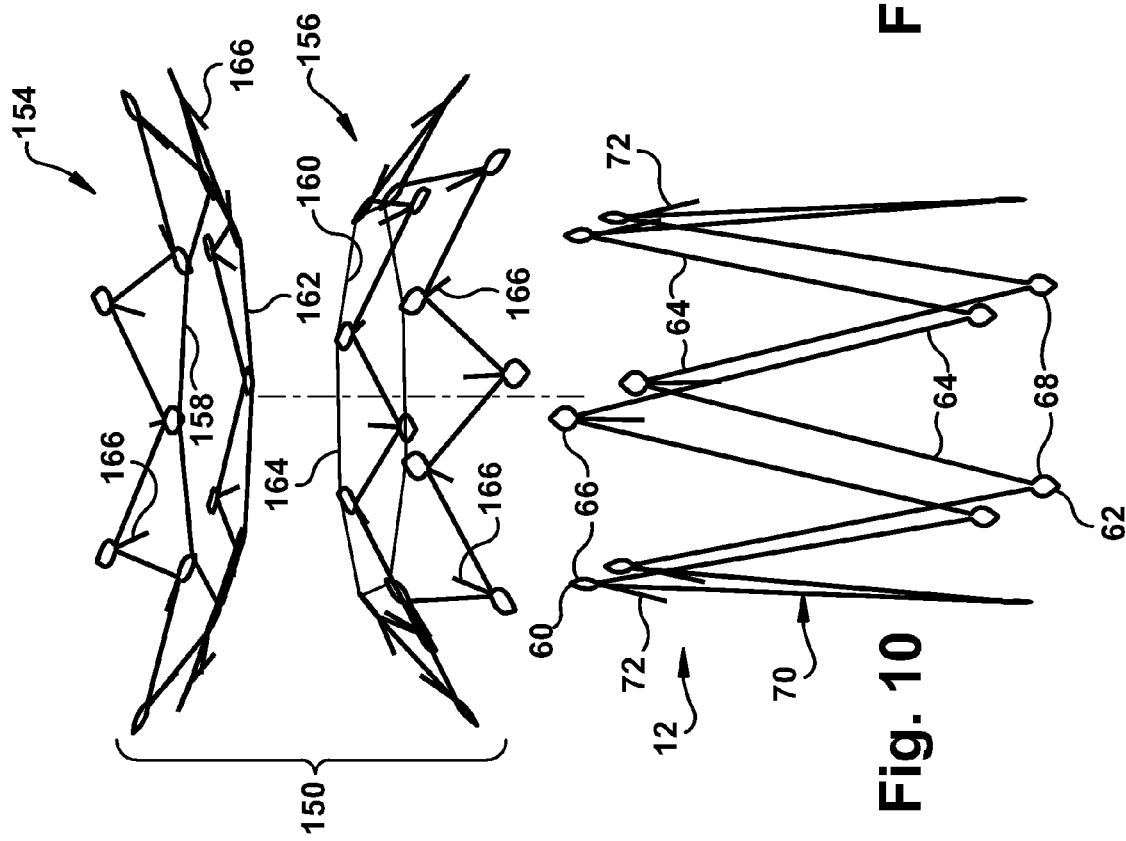

US 8,845,722 B2

HEART VALVE PROSTHESIS AND METHOD OF IMPLANTATION THEREOF

TECHNICAL FIELD

The present invention relates to a heart valve prosthesis and to a method of implanting the prosthesis.

BACKGROUND

Various types of heart valve prostheses have been developed to replace the patient's native valve exhibiting valvular disease or dysfunction. Valve replacement offers requires open heart surgery, although more minimally invasive procedures (e.g., percutaneous implantation) may be utilized for replacing certain valves. Heart valve prostheses typically are either mechanical valve designs or biological designs.

The type of heart valve prosthesis and method of implantation are often dictated according to which valve requires replacement and the size of the valve. For example, a mitral valve is often larger than 23 millimeters, making various mechanical and many types of pericardial valves inadequate for replacement. Additionally, because of the large size, in order to have a functioning and effective replacement valve, the replacement procedure cannot be done percutaneously or using a traditional catheter.

SUMMARY

The present invention relates to a heart valve prosthesis and to methods of implanting the prosthesis, such as at the mitral or aortic position.

One aspect of the invention provides a heart valve prosthesis comprising a supported valve that includes a biological valve portion mounted within a support structure. The supported valve is configured to provide for substantially unidirectional flow of blood through the supported valve. The supported valve has inflow and outflow ends that are spaced axially apart from each other. A fixation support member includes inflow and outflow portions. The inflow portion of the fixation support member extends from a radially inner contact surface of the fixation support member radially outwardly and axially in a direction of the inflow end of the supported valve. The outflow portion of the fixation support member extends from the radially inner contact surface radially outwardly and axially in a direction away from the inflow portion of the fixation support member. The radially inner contact surface is attached to a radially outer surface of the supported valve adjacent the inflow end of the supported valve. The supported valve and the fixation support member are deformable between a reduced cross-sectional dimension and an expanded cross-sectional dimension thereof, whereby implantation of the heart valve prosthesis is facilitated.

Other aspects of the invention relate to methods of implanting the prosthesis at a valve annulus (e.g., a mitral valve annulus or aortic valve annulus) during a low invasive procedure.

BRIEF DESCRIPTION OF THE DRAWINGS

FIG. 1 is an exploded view depicting examples of support structures that can be utilized in a heart valve prosthesis according to an aspect of the invention.

FIG. 2 is an exploded view of a heart valve prosthesis according to an aspect of the invention.

FIG. 8 depicts an example of the heart valve prosthesis being implanted at the mitral position through the heart muscle according to an embodiment of the invention.

FIG. 9 depicts an example of the heart valve prosthesis being implanted at the mitral position through an atrial appendage according to another embodiment of the invention.

FIG. 10 depicts an example of support structures that can be utilized in another embodiment of the heart valve prosthesis.

FIG. 11 is an exploded view of a heart valve prosthesis according to another embodiment of the invention.

DETAILED DESCRIPTION

Figure 3:
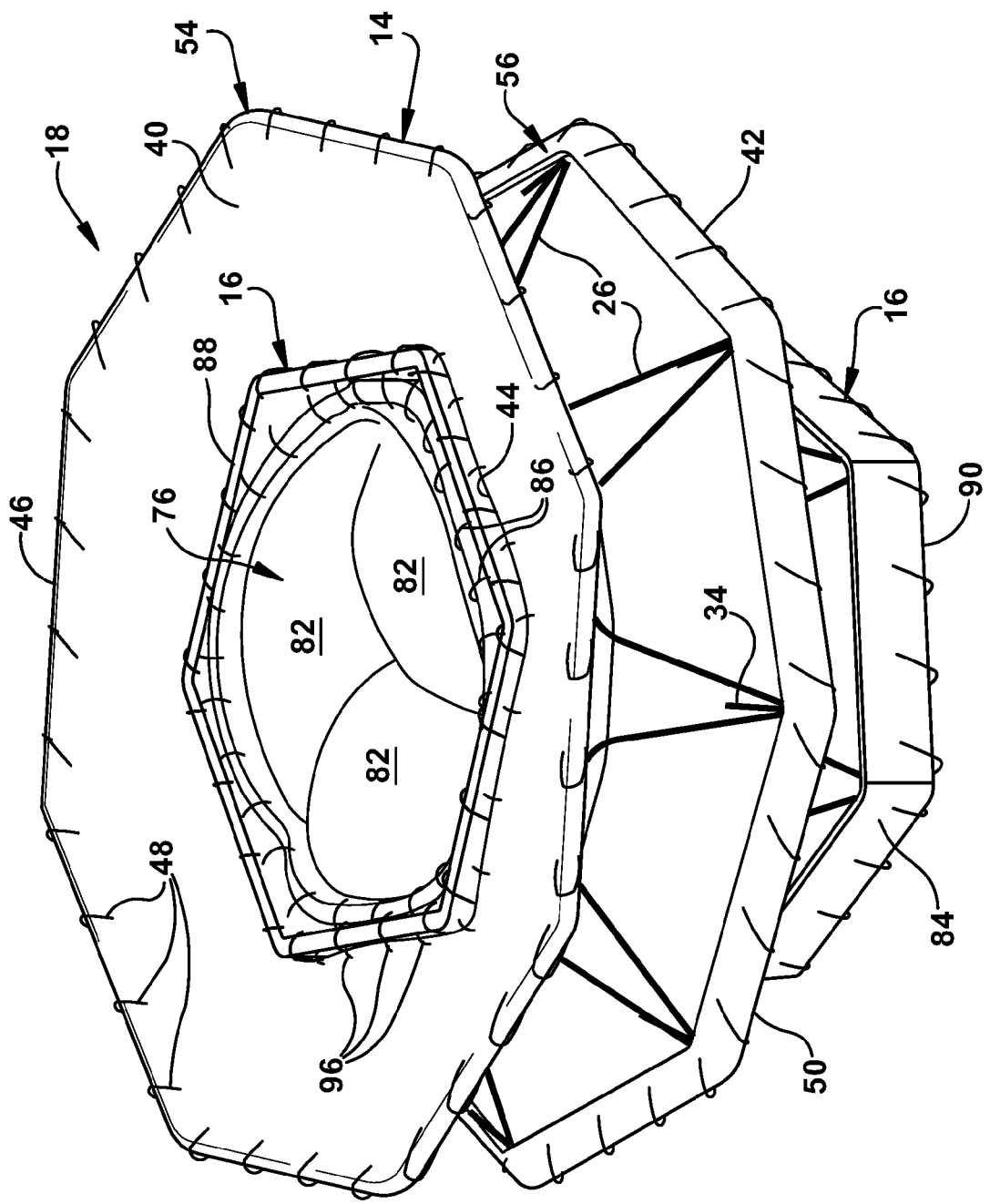
FIG. 3 depicts an example of a heart valve prosthesis according to an aspect of the invention.

The invention relates generally to a heart valve prosthesis that includes a fixation support member dimensioned and configured to facilitate implantation using low invasive procedures. The prosthesis is well suited for implantation at an atrio-ventricular position. For example, the prosthesis can be made in larger sizes (e.g., greater than 24 mm) often required for mitral valve replacement. The prosthesis and methods can also be utilized for replacement of the aortic valve.

FIG. 1 depicts an example of support structures 10 and 12 that can be utilized in a heart valve prosthesis. In this example, the support structure 10 is utilized to anchor or help hold the prosthesis in a desired axial position relative to the heart valve annulus when implanted. The support structure 12 is utilized to support the valve in a desired orientation, which support can vary according to the type and configuration of heart valve implemented in the prosthesis. Thus, the support structure 10 is utilized to form a fixation support member 14, such as shown in FIG. 2, and the support structure 12 can be utilized (e.g., as a stent) to support a valve portion and provide a supported heart valve 16, as shown in FIG. 2. Accordingly, as used herein, the support structure 10 may be referred to as a fixation support structure and the support structure 12 may be referred to as a valve support, such as a stent.

The fixation support structure 10 can be implemented as a flexible and deformable annular support that can be deformed to a reduced cross-sectional dimension and then expanded to its original, fully expanded, cross-sectional dimension, such as shown in FIG. 1. The fixation support structure 10 includes an inflow portion 20 and an outflow portion 22. An annular opening extends through the support structure 10 corresponding to a radially inner extent thereof, indicated at dashed line 28, of the support.

In the example of FIG. 1, each of the inflow and outflow portions 20 and 22 includes a plurality of support features 24 and 26, respectively. In example FIG. 1, the inflow support features 24 extend radially outwardly and axially from the inner extent 28 toward in an inflow direction. Conversely, the outflow support features 26 extend from the inner extent 28 radially outwardly and axially toward an outflow direction (e.g., in the opposite axial direction from the inflow support features). Each of the inflow support features 24 extends from the radially inner extent 28 and terminates into a corresponding distal end 30 thereof. Similarly, each of the outflow support features 26 also extends from the radially inner extent 28 to terminate in a respective distal end 32. Thus, each pair of adjacent support features 24 extend toward each other and are interconnected at a juncture corresponding to the distal end 30, while support features 26 can be formed of a pair of adjacent supports that extend toward each other and are connected at a juncture corresponding to the distal end 32. The respective junctures can be biased (e.g., configured as springs) to urge each of the associated legs apart to maintain the support structure 10 in its expanded condition. In the example of FIG. 1, there are eight junctures at each of the respective ends 30 and 32 that are interconnected by associated support features. Those skilled in the art will understand and appreciate that other numbers (e.g., 6, 7, 9, 12 and so forth) and configurations of end junctures can be utilized.

As a further example, the fixation support structure 10 can be configured as a continuous monolithic structure, such as shown in FIG. 1. Thus, the support features 24 and 26 alternate between extending in the inflow and outflow directions along the circumferential path corresponding to the radially inner extent 28 of the support structure 10. By way of example, the fixation support structure 10 can be formed from a stent similar to the valve support structure 12 (having a zigzag arrangement of support features) in which the distal ends 30 and 32 are bent radially outwardly while a substantially central annular portion is maintained at the original diameter. Alternatively, an axially central annular portion of a larger diameter cylindrical support (having the zigzagging support features) can be reduced to a desired inner diameter of the radially inner extent, such as by a suture or other means. Other types and configurations of supports can also be utilized (see, e.g., FIGS. 10-13).

Due to the structural arrangement of support features 24 and 26 that define the respective inflow and outflow portions 20 and 22 of the fixation support structure 10, it is thus shown that the fixation support provides a generally hourglass shape in which it has a substantially V-shaped cross-sectional configuration for a longitudinal cross-section taken radially outwardly through one side of the fixation support in its expanded configuration of FIG. 1.

The inflow and outflow portions 20 and 22 can also include one or more projections or spikes 34. For instance, the spikes 34 can extend from the distal ends 30, 32 of the support features 24 and 26 toward an opposing one of the outflow or inflow portion 22 or 20 of the support structure 10. For instance, spikes from the inflow portion 20 extend from the distal end portion 30 axially away from the support feature 24 toward the opposing outflow portion 26. Similarly, spikes from the outflow portion 22 extend from the distal end portion 32 axially away from the support feature 26 toward the opposing inflow portion 20. Various numbers and arrangements of spikes 34 can be implemented, such as single spike or more than two spikes at some or all of the ends 30 and 32. Additionally, ends of the spikes 34 can have tapered or sharpened and/or barbed tips to facilitate gripping surrounding tissue when implanted.

As depicted in FIG. 2, the fixation support member 14 can include one or more web 38 of flexible biocompatible material that is attached over and covers the respective inflow and outflow portions 20 and 22. The material can be a natural or biological material (e.g., a sheet of fixed and detoxified animal pericardium, dura matter) or it can be a synthetic biocompatible material (e.g., a sheet of synthetic bioabsorbable polymer, such as e-PTFE).

The web 38 can include an inflow web portion 40 that covers an inflow extent of the support features 24, as well as an outflow web portion 42 that covers the outflow support features 26. For example, the inflow web portion 40 of the fixation support member 14 can extend from a radially inner contact surface 44 (e.g., corresponding to the radially inner extent 28 of FIG. 1) and extend over and engage the support features 24 to terminate at an inflow distal end 46 of the support member 14. Thus, the surface of the support features 24, as exposed in an inwardly axial direction, is completely covered. The distal end 46 can be defined by a seam as the end of the inflow web 40 is folded over the distal end portions 30 of the support features 24. The folded over ends can be attached together by corresponding sutures 48.

The outflow web 42 can be similarly configured as extending from the radially inner contact surface 44 to define a distal outflow edge 50 of the outflow portion of the fixation support member 14. The edge 50 can be defined by folding the end of the web over the distal end portions 32 of the outflow support features 26 and attaching the ends together by corresponding sutures 52. For example, the folded over portion of the inflow and outflow webs 40 and 42 can be folded over so as to leave each of the respective spikes 34 to be exposed and facilitate their insertion and gripping tissue when the resulting prosthesis is implanted.

The inflow web 40 covering the inflow portion 20 of the fixation support structure 10 thus corresponds to an inflow portion 54 of the completed fixation support member 14. Similarly, the outlfow web 42 covering the outflow portion 22 of the fixation support structure 10 thus corresponds to an outflow portion 56 of the fixation support member 14. It is to be understood that the respective webs 40 and 42 can be constructed of a single sheet of pliant biocompatible material or from multiple sheets to form the web 38.

Referring back to FIG. 1, the valve support structure 12 includes axially spaced apart ends 60 and 62 interconnected by generally axially extending support features 64. In the example of FIG. 1, adjacent pairs of support features 64 are interconnected by arcuate junctures 66 and 68 at the respective ends 60 and 62 so as to define a generally sinusoidal or zigzag shaped sidewall portion 70 arranged in a generally cylindrical configuration. In the example of FIG. 1, there are six junctures 66 and 68 at each of the respective ends 60 and 62 that are interconnected by associated support features 64. Those skilled in the art will understand and appreciate that other numbers (e.g., 2, 5, 8, 12 and so forth) and configurations of end junctures 66, 68 can be utilized in accordance with an aspect of the present invention. For example, as an alternative to curved interconnecting end junctures 66, 68 shown in FIG. 1, such ends could be pointed or rectangular or be implemented as coil springs.

The support structure 12 further includes one or more projections or spikes 72 that extend axially and radially outwardly from the end juncture 66, corresponding to the inflow end of the support. While a pair of such spikes are illustrated as associated with each end juncture 66, 68, other number of spikes can be implemented, such as single spike or more than two spikes at some or all of the junctures. The spikes 72 operate to mitigate axial movement of the prosthesis when implanted, such as by having each spike 72 forming an acute angle relative to its associated support feature 64 from which it extends.

By way of further example, one or both of the support structures 10 and 12 may be formed of a shape memory alloy material, such as may be formed of a nitinol (nickel-titanium alloy) wire. Shape memory (or thermal memory) is a characteristic in which a deformed part remembers and recovers to a pre-deformed shape upon heating or application of another stimulus. By forming the support structures 10 and 12 of a shape memory alloy, the structures are inelastically deformable to new shape, such as a reduced cross-sectional dimension, when in its low-temperature (martensitic) form. For example, the prosthesis 18 (FIG. 3) may be cooled, such as by being introduced to a cooling solution (e.g., water), and then compressed to a desired reduced cross-sectional dimension to facilitate insertion into an implanter. Typically when compressed the inflow and outflow portions will be urged radially inwardly to a diameter that is less than an outer diameter of the supported valve in its expanded condition.

When the prosthesis 18, which includes support structures 10 and 12, is heated to its transformation temperature, which may vary according to the alloy composition, it quickly reverts to its high-temperature (austenitic) form. The prosthesis thus may retain the compressed condition by keeping it cooled. Alternatively, the stent and valve may be retained in the compressed position, such as with sutures circumscribing the structure, a cylindrical enclosure (e.g., barrel of an implanter) around the structure, etc. The prosthesis 18 will then return toward its high-temperature (or original) position upon removal of the retaining element.

It is to be appreciated that, alternatively, the support structures 10 and 12 could be formed of inelastically deformable materials so as to require an intervening physical force to return the deformed stent substantially to a desired configuration. For example, a balloon catheter or spring mechanism could be employed to urge the support structures 10 and 12 and the valve 76 located therein generally radially outward so that, after being implanted to a desired position, the stent will engage the surrounding tissue in a manner to inhibit movement relative to the surrounding tissue.

Returning to FIG. 2, the supported valve 16 includes a heart valve 76 mounted within the valve support structure 12. The valve 76 includes an inflow end 78 and an outflow end 80 at axially opposed ends of the valve, with a sidewall portion extending between the ends thereof. The inflow end 78 of the valve 76 is positioned near an inflow end 60 of the support structure 12. A plurality of leaflets 82 extend radially inward from the valve wall and coapt along their adjacent edges to provide for substantially unidirectional flow of blood through the valve 76. The outflow end 80 of the valve 76, which is located near the outflow end 62 of the support, can have a generally sinusoidal contour, such as shown in FIG. 2. The peaks of the sinusoidal outflow end (corresponding to commissures of leaflets) can be aligned generally with and attached to support junctures 66 at the inflow end 62 of the support structure 12. The valve 76 can be connected within the support structure 12 via sutures or other known connecting means, for example.

It is to be understood and appreciated that various types of valve configurations of could be utilized for the supported valve 16. For example, the valve 76 can be formed of biological material and include one or more leaflets mounted within a length of tubular valve wall or other generally cylindrical biocompatible material and operate in a known manner to provide for the unidirectional flow of fluid through the valve from the inflow to outflow ends. As one example, when the prosthesis is to be implanted at the mitral position, the valve 76 can be a treated porcine mitral valve (e.g., homograft or xenograft). While porcine valves have been recognized by the inventor as being effective, those skilled will understand that other animal heart valve can be utilized, such as bovine, equine or the like.

If the valve portion 76 is formed of a natural biological material, such as an animal heart valve, a venous valve, or a composite valve manufactured of natural tissue, the valve can be chemically fixed, such as in a suitable solution of glutaraldehyde in a closed condition (as is known in the art). The fixation process facilitates closure of the valve 76 under application of back flow pressure, while remaining open during normal forward blood flow through the valve 76. By way of example, the natural tissue valve may be cross-linked with glutaraldehyde and undergo a detoxification process with heparin bonding, as to improve biocompatibility of the valve 76 and mitigate calcification and thrombus formation.

As a result of such fixation, the valve portion 76 exhibits structural memory. That is, if the valve 76 is compressed, such as to a reduced diameter at the time of being implanted, it will return substantially to its original shape and configuration upon removal of radially inward forces. As a result, the valve 76 is able to maintain coaptation of the leaflets 82 even after being deformed. The memory feature of the valve is further augmented by mounting it within the valve support structure (or stent) 12, such as shown and described herein.

In the example of FIG. 2, the ends 60 and 62 of the valve support structure 12 are covered with one or more sheet 84 of a pliant and biocompatible material that provides an outer sheath for the supported valve 16. The outer sheath mitigates contact between the blood and the support when the prosthesis is implanted. The biocompatible material can be a nature material (e.g., animal pericardium, dura matter) or a synthetic material (e.g., synthetic pericardium substitute, such as a bioabsorbable polymer). The outer sheath can be the same material as the web 38 for the fixation support member 14 or it can be a different material.

For instance, the sheet 84 can be attached to a radial outer surface of the valve 76 and placed over the inflow and outflow ends 60 and 62 by folding the material over the ends of the support features 64. The folded over ends can be attached together by corresponding sutures 86 applied at each of the respective inflow and outflow ends of the supported valve 16. The seam of the folds at each of the respective ends can thus define the inflow end 86 and the outflow end 88 of the supported valve 16. Alternatively, the outer sheath can cover the entire outer surface of support structure 12, such that all non-biological material is completely covered, for example.

Figures 4, 5:
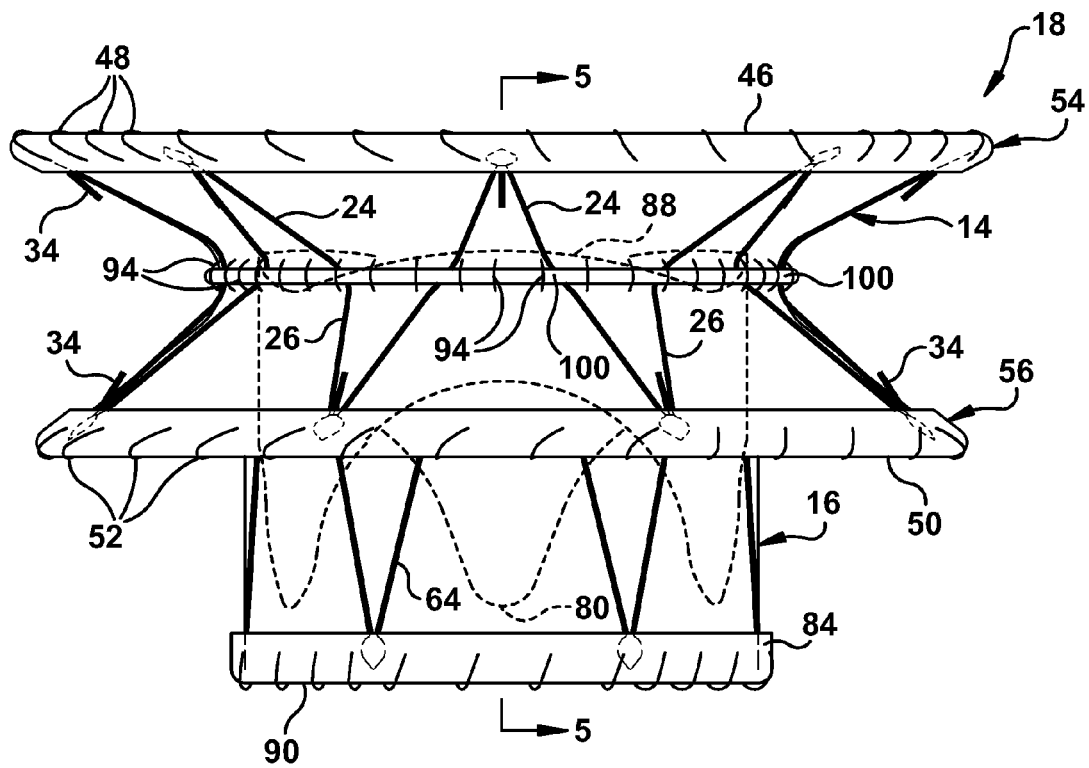
FIG. 4 is a side elevation of the heart valve prosthesis of FIG. 3.
FIG. 5 is a cross-sectional view of the prosthesis in FIG. 4, taken along line 5-5.

FIGS. 3, 4 and 5 depict a heart valve prosthesis 18 constructed from the fixation support member 14 and the supported valve 16 shown and described with respect to FIG. 2. Accordingly, the same reference numbers are utilized to identify features already introduced. As described herein, the prosthesis 18 is deformable between a reduced cross-sectional dimension and an expanded cross-sectional dimension thereof, such that implantation of the heart valve prosthesis is facilitated.

The fixation support member 14, including the inflow and outflow portions 54 and 56 thereof extend outwardly from the supported valve 16 adjacent an inflow end 88 of the supported valve. As best shown in FIGS. 3 and 5, the radially inner contact surface 44 of the fixation support member 14 is attached to a radially outer sidewall surface of the supported valve 16 adjacent the inflow end thereof. The attachment can be made by sutures, or other means of attachment such as surgical adhesives, staples. For example, the radially inner contact surface 44 can be secured to the folded over outer sheath 84 at the inflow end. Alternatively, the radially inner contact surface 44 can engage the sidewall just below the edge of the outer sheath 84 so that the folded over outer sheath, having two layers provides addition structure for suturing the fixation support member to the supported valve 16.

As shown in the example of FIGS. 4 and 5, sutures 94 can be applied to attach the radially inner contact surface 44 at the inflow end of the supported valve 16. The arrangement of sutures 94 can be applied externally to help hold and maintain the desired axial position of the fixation support member 14 relative to the supported valve 16. Additional sutures 96 can be applied to further secure the inflow end of the supported valve 16 to the adjacent portion of the inflow web 40, along the entire perimeter thereof, such as shown in FIGS. 3 and 5.

Additionally, to help maintain a desired diameter of the radially inner contact surface 44 of the fixation support member 14, a cord (e.g., a suture or other retaining mechanism) 100 can be applied externally at the juncture of the inflow and outflow portions 20 and 22. The cord 100 can be applied around the support structure 10 before or after the web covering 38 is attached. Alternatively, or additionally, the dimensions of the radially inner contact surface 44 can be set by structural or material properties utilized to form the support structure 10, such that no cord 100 is required.

In the cross-sectional view of FIG. 5, it is shown that a longitudinal cross-section through the prosthesis 18 demonstrates a substantially V-shaped cross-sectional configuration of the fixation support member 14 in its expanded cross-sectional dimension. For instance, the radially inner contact surface 44 defines an apex and each of the inflow and outflow portions of the fixation support member define legs of the V-shaped cross-sectional configuration. It will be appreciated that the term "substantially" as used in relation to the V-shaped configuration is intended to encompass that the apex of the "V" can be curved or arcuate (as shown in FIG. 5) as well as being pointed. Additionally, the legs of the V-shaped configuration do not need to perfectly straight, but can be curved provided that distal ends of the inflow and outflow portions are axially spaced apart to enable tissue to be received therebetween when implanted. The space between the legs of the V-shaped cross-sectional configuration defines a receptacle, indicated at 102, dimensioned and configured for receiving tissue therein. For the example of FIGS. 2-5, the receptacle 102 has a generally toroidal shape. It will be understood that the fixation support member 14 may be implemented with or without the web or other covering or with a different covering that is not continuous, as in the examples of FIGS. 3-5.

As also depicted in the example of FIG. 5, the inflow portion 54 is separated from the outflow portion 56 in its expanded condition by an angle equal to the sum of angles $\theta_1$ and $\theta_2$, each of which is drawn relative to a plane 104 that extends through the prosthesis 18 transverse to the longitudinal axis thereof. The combined angle of $\theta_1+\theta_2$ is greater than 40°, and typically ranges between 70 and 100°. Additionally, $\theta_2$ can be greater than $\theta_1$ to better accommodate receiving native tissue for implantation of the prosthesis 18 at the mitral position.

Since according to one embodiment the prosthesis 18 can be implanted at the mitral position, the supported valve 16 can be provided with a diameter or size that is greater than 23 millimeters, such as ranging from about 25 millimeters to about 34 millimeters, or even larger. Also depicted in FIG. 5, in its expanded condition, the respective spikes 34 of fixation support member 14 extend outwardly from the inflow and outflow portions 54 and 56 into the space 102 toward the opposite outflow and inflow portions to facilitate insertion and fixation of the fixation support member in tissue when implanted.

Figure 6:
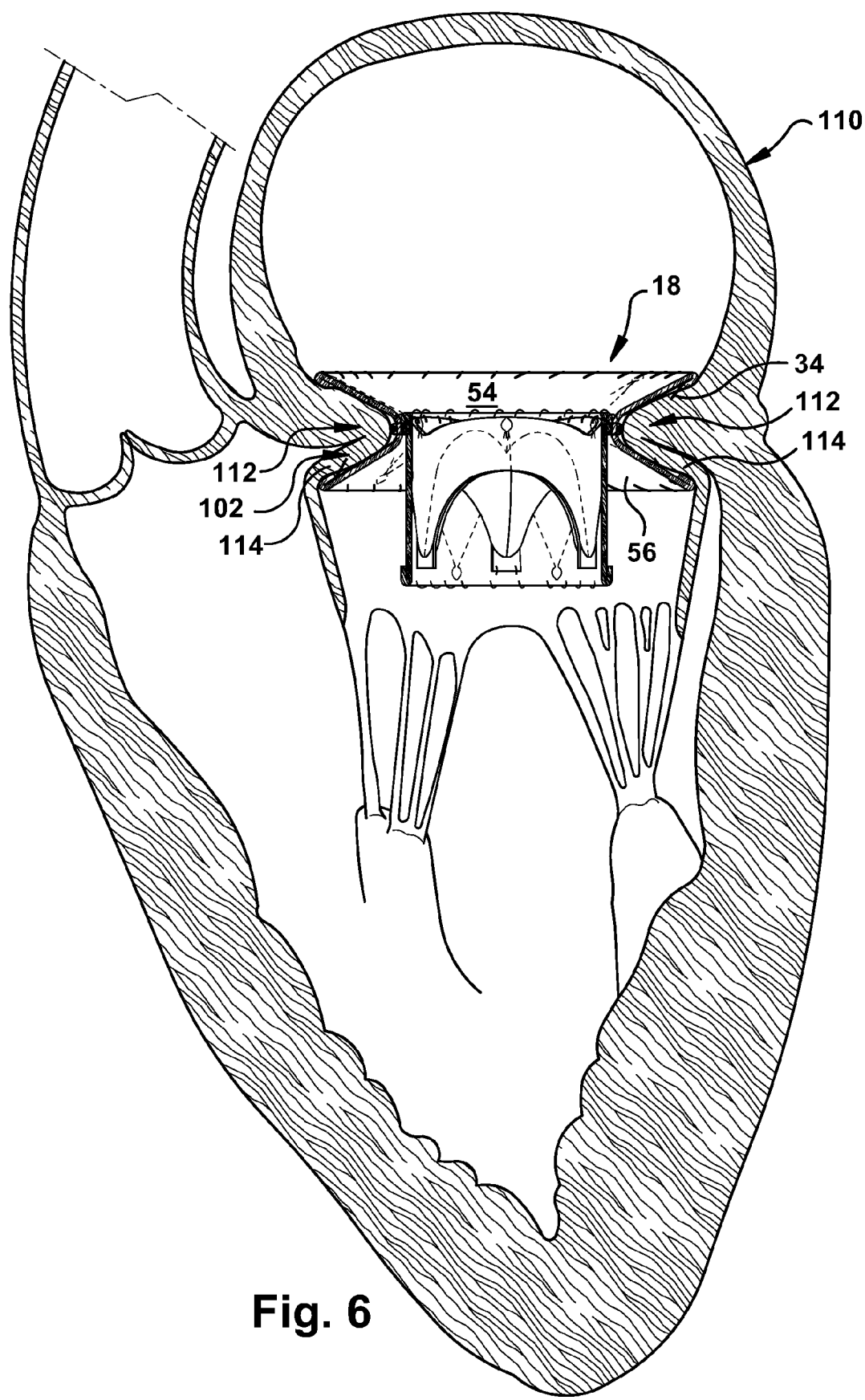
FIG. 6 depicts an example of a heart valve prosthesis implanted at the mitral position.
Figure 7:
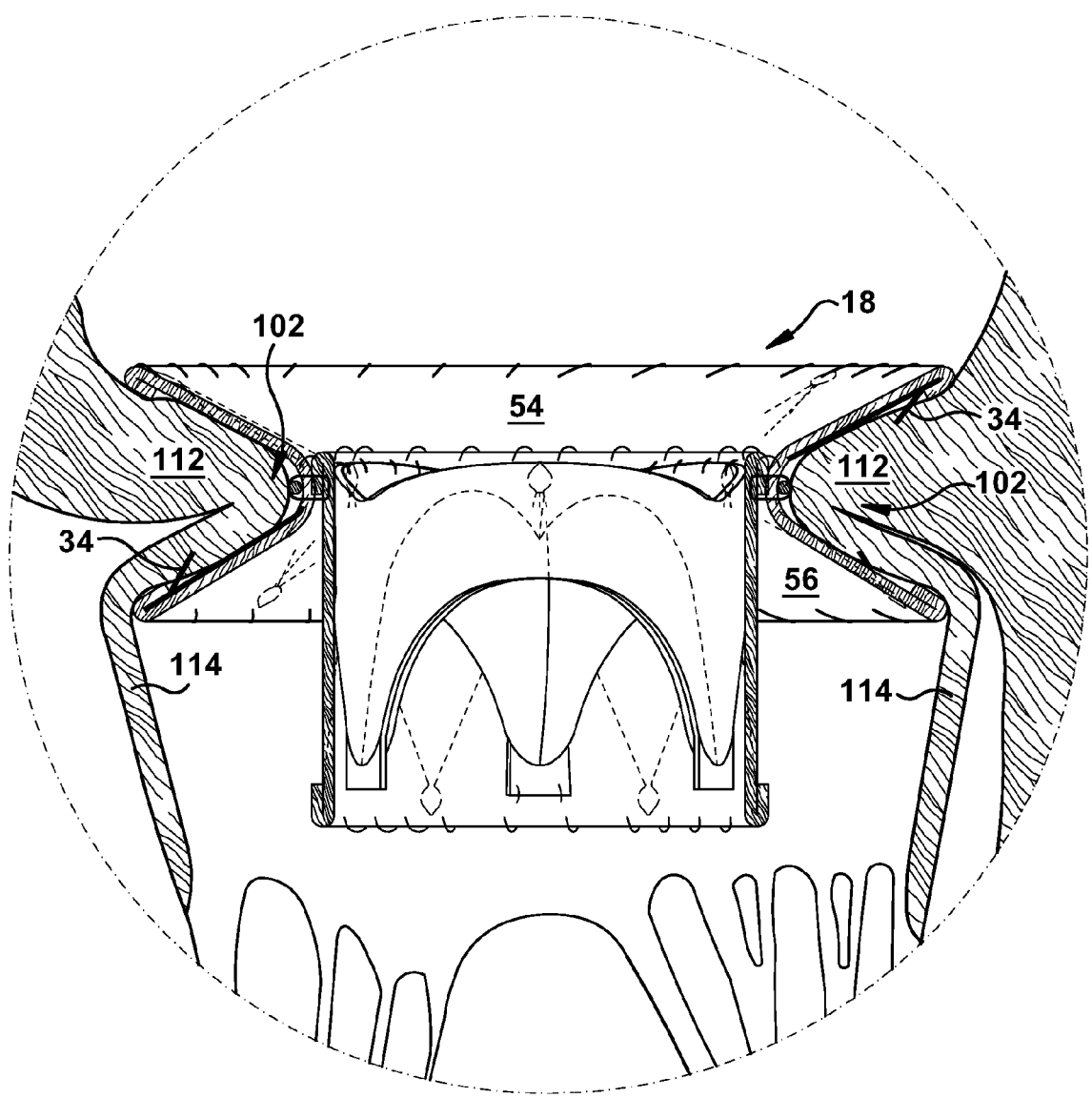
FIG. 7 is an enlarged view of the implanted prosthesis of FIG. 6 demonstrating its attachment at the mitral valve annulus.

FIGS. 6 and 7 depict an example of the prosthesis 18 implanted at the mitral position in a patient's heart 110. FIG. 7 is an enlarged view of the implanted prosthesis 18 from FIG. 6. As shown in FIGS. 6 and 7, the space 102 between the inflow and outflow portions 54 and 56 of the fixation support member 14 provides a receptacle for receiving therein tissue at the mitral valve annulus 112. Thus, the annulus 112, including portions of the patient's native valve 114, can fit within the corresponding receptacle space 102 formed between the opposing surfaces of the inflow and outflow portions 54 and 56 to help hold the prosthesis 18 at the desired mitral position without requiring the use of sutures. Of course, one or more sutures (not shown) can be applied to further affix the prosthesis.

Also demonstrated in FIGS. 6 and 7, the spikes 34 can extend outwardly from the inflow and outflow portions 54 and 56 and, in turn, grippingly engage the respective native annulus tissue at the inflow end of the mitral valve and the patient's native valve leaflets 114 at the outflow portion. Additional spikes from the inflow end of the supported valve can also help fix and anchor the prosthesis 18 at the mitral position.

As described herein, the prosthesis 18 can be implanted in a low invasive procedure, which may include no cardio pulmonary bypass or may be implemented with a reduced amount of cardio pulmonary bypass relative to other mitral valve replacement procedures. Additionally, when implanted, the prosthesis 18 can be implanted without removing the patient's native mitral valve, as shown. However, the prosthesis can also be implanted if the patient's value is removed (wholly or partially).

Another embodiment of the invention provides for a method for implanting a heart valve prosthesis. For consistency of explanation and not by way of limitation, the methods will be described with respect to the example embodiment of the prosthesis of FIGS. 3-5 and implanted at the mitral position as depicted with respect to FIGS. 8 and 9. It will be appreciated that other configurations of prosthesis (including FIGS. 12-13 and other designs) can be implanted according to the methods described herein. Additionally, while the methods of FIGS. 8 and 9 are described with respect to implanting the prosthesis 18 at the mitral position, the methods can be adapted for implantation at the aortic position. Thus, the prostheses shown and described herein are applicable for implantation at any atrio-ventricular position.

At some time prior to implanting the valve at the desired implantation site, for each of the approaches of FIGS. 8 or 9, the heart valve prosthesis 18 is inserted into a barrel 120 of an implanter, such that the prosthesis has the reduced cross-sectional dimension relative to the expanded cross-sectional dimension of the prosthesis. The implanter can be of the type shown and described with respect to FIG. 19 of U.S. patent application Ser. No. 10/266,380, filed on Oct. 8, 2002, and entitled HEART VALVE PROSTHESIS AND SUTURELESS IMPLANTATION OF A HEART VALVE, which is incorporated herein by reference. The implanter in the above-incorporated patent application provides a substantially linear barrel, which can have a flexible or bendable tip to facilitate direct implantation through the heart to the desired implantation site. This type of implanter is especially well-suited for mitral valve replacement over catheters or other percutaneous types of implanters due to the large diameter of typical native mitral valves. Other types of implanters may also be employed for performing the methods described herein.

Returning to the example of FIG. 8, before inserting the barrel 120 into the patient's heart 110, an opening 122 is created in the patient's heart 110 to provide a substantially direct path to a valve annulus 112 in the patient's heart 110. As used herein, the term "substantially" as modifier for "direct path" is intended to convey that the opening is intended to provide a line-of-sight path from the opening to the implantation site, although some deviation might exist.

Such deviation can be compensated, for instance, by employing a bendable barrel 120 that can be inelastically deformed to a shape to facilitate implantation at the site or by deforming the heart manually during the procedure to provide the corresponding path along which the barrel can traverse. This is to be contrasted with percutaneous implantation procedures that are performed through femoral vein, for example.

As a further example, a mattress suture, or other type of purse string suture 127 can be applied at location in the patient's heart through which the implanter is to be inserted. In the example of FIG. 8, the location comprises the patient's heart muscle located at the apex 126 of the heart 110. Two ends of the purse string 127 suture extend from the apex tissue can be tightened around the barrel 120 to mitigate blood loss. Consequently, cardiopulmonary bypass is not required. However, it is to be understood that in certain situations, some bypass may be necessary, although usually for a much shorter period of time than with conventional procedures.

As shown in FIG. 8, the barrel 120 of the implanter has been inserted through the apex 126 of the patient's heart 110. For instance, the valve of the prosthesis 18, in its reduced cross-sectional dimension, can have a diameter of 15 mm to 20 mm for implanting a valve having a 24-35 mm fully expanded diameter. Those skilled in the art will appreciate that valve dimensions (e.g., ≥24 mm) are not suitable for percutaneous implantation procedures. However, such sizes of valves are deemed appropriate and sometimes necessary for replacement of the mitral valve. Additionally, many existing manufactured pericardial valve designs designed for minimally invasive percutaneous implantation are not effective at such large sizes and/or are not capable of operating under the hemodynamic conditions that typically exist for the mitral position.

During a closed heart procedure, the insertion of the implanter can be guided by a patient's finger (or other instrument) 128 that is introduced via the left atrial appendage 130. A purse string or mattress suture 132 can be applied around the atrial appendage to mitigate blood loss. The surgeon's finger can locate the patient's native valve and associated annulus 112 to help position and guide the distal end of the implanter to the desired implantation site. Once at the desired site, the valve can be discharged from the barrel 120 of the implanter and the implanter withdrawn from the heart 110. The finger (or other instrument) 128 can also be used help guide the valve to ensure its fixation and implantation at the appropriate position at the mitral annulus 112, such as shown in FIGS. 6 and 7.

After the prosthesis 18 has been expanded to its expanded cross-sectional dimension (See FIGS. 6 and 7), which may be performed automatically by expansion of the valve or by manual means such as the balloon catheter or other mechanism for expanding the prosthesis, the valve is fixed at the desired position. As described herein, one or more sutures can be applied externally through the heart 110 to help anchor the prosthesis 18 at the desired implantation position. Alternatively, a trocar or other device can be inserted through the left atrial appendage 130 or otherwise to provide a suture or other means for further securing the prosthesis 18 at such position.

FIG. 9 depicts part of an implantation method in which the barrel 120 of the implanter and prosthesis 18 are inserted through the left atrial appendage 130 for direct implantation at the mitral annulus 112. The steps up to insertion of the barrel into the atrial appendage 130 are similar to those described with respect to FIG. 8. Briefly, the chest is opened, a purse string suture 132 applied about the atrial appendage 130 and the barrel 120 is inserted through the opening through the atrial appendage. The purse string 132 can be tightened about the barrel to mitigate blood loss, thereby allowing the absence of cardio pulmonary bypass.

In order to facilitate proper positioning of the prosthesis 18, a positioning apparatus (e.g., a dilator or umbrella or other structure) 136 can be inserted through the heart muscle, such as the apex 126 of the patient's heart 110, and positioned to a desired location. A purse string suture 127 can be employed at the apex 126 and tightened around the instrument to control bleeding. The placement of the positioning apparatus 136 can be guided by fluoroscopy or other imaging modalities.

By way of example, positioning apparatus 136 can include an umbrella-type distal end 138 that is attached to a shaft 140. The distal end 138 can be inserted in a closed condition through the apex 126 to a desired position the patient's heart valve and expanded to an open condition. In the open condition, the distal surface of the opened umbrella 138 provides a back stop against which the discharge end of the barrel 120 or prosthesis 18 can engage for defining an implantation position. For instance, once the barrel 120 of the implanter engages the distal end 138, which can be felt or otherwise perceived by the surgeon, the prosthesis 18 can be discharged from the barrel at the mitral valve annulus. When expanded, the inflow and outflow portions 54 and 56 of the fixation support member 14 can receive tissue at the mitral annulus and thereby hold the prosthesis 18 at a fixed axial position relative to the mitral annulus 112, as shown in FIGS. 6 and 7.

Figure 12:
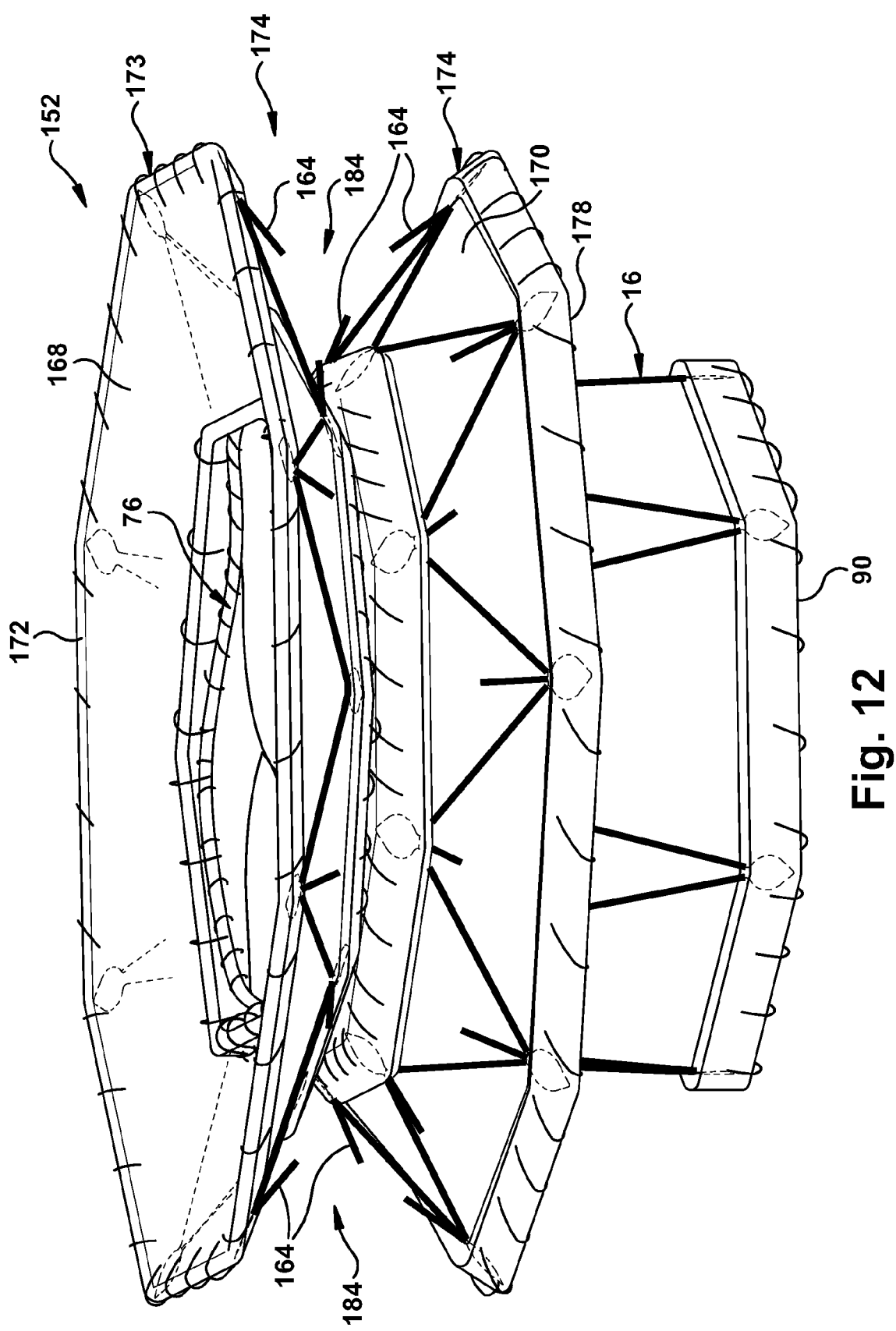
FIG. 12 is an example of the constructed valve from FIG. 11.
Figure 13:
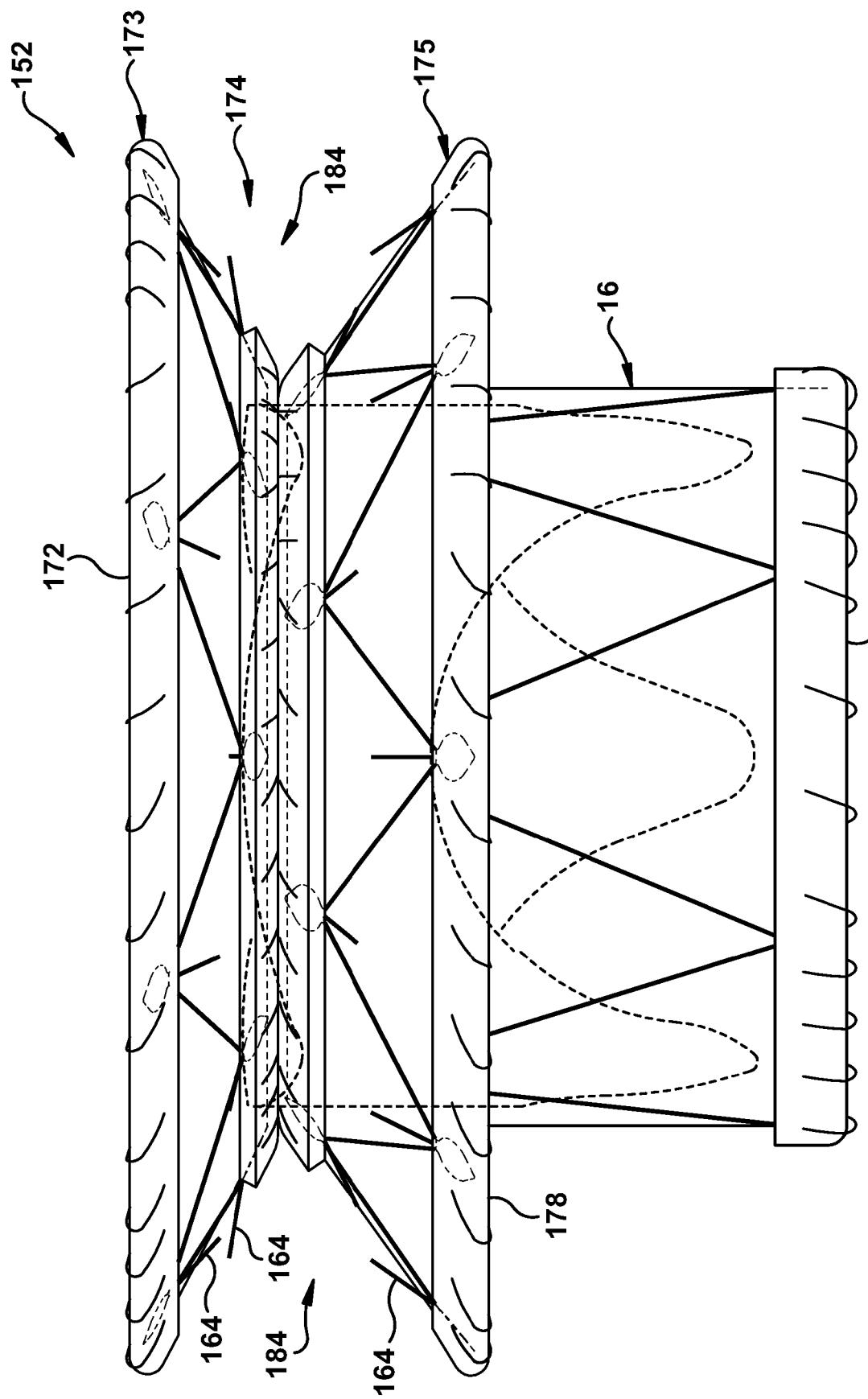
FIG. 13 is a side elevation of the valve of FIG. 12.

FIG. 10 demonstrates another embodiment of example of support structures that 150 and 12 can be utilized to provide a heart valve prosthesis 152 (See FIGS. 12 and 13). In the example of FIG. 10 the valve support structure 12 is identical to the structure shown and described with respect to FIG. 1. Accordingly, reference can be made back to the corresponding description in FIG. 1 for additional information about the valve support structure 12.

In the example of FIG. 10, the fixation support structure 150 is formed of separate inflow and outflow support structures 154 and 156 that can be utilized to provide a corresponding fixation support having the appropriate dimensions and configuration for use with the prosthesis. As an example, each of the respective inflow and outflow support structures 154 and 156 can be formed of a stent or other supporting structure (e.g., similar to the stent or support structure 12 utilized to form the supported valve 16). Each support structure 154 and 156 can have a substantially frusto-conical configuration and a respective opening 158 and 160 that extends therethrough. A maximum diameter of each support structure 154 and 156 is greater than the outer diameter the supported valve 16 for which it is to be utilized. The diameter of each opening can approximate the outer diameter the supported valve 16. Each support structure 154 and 156 thus can have a generally sinusoidal or zigzag sidewall pattern of support features extending axially and radially outwardly from the respective opening 158 and 160 to its opposing end.

For example, one end of each support structure 154 and 156 can be reduced to a diameter of the opening, such as by applying a cord 162 and 164 to reduce the respective openings 158 and 160 to a desired diameter. The cords 162 and 164 thus can be utilized to selectively provide the radially inner dimension of the inflow and outflow support structures 154 and 156 to a desired diameter for each such portion. Typically, the diameters of the openings 158 will be substantially the same. Those skilled in the art will appreciate other ways to achieve desired dimensions and configuration for each of the support structure 154 and 156, which can include structurally constructing the support structures or using other means for reducing one of the ends.

Each of the inflow and outflow support structures 154 and 156 for the fixation support member can include spikes 166 that extend outwardly from the distal (larger diameter) ends, such as shown in FIG. 10. Various numbers and configurations of the spikes 166 can be implemented, such as single spike or more than two spikes at some or all of the ends. Additionally, ends of the spikes 166 can have tapered or sharpened and/or barbed tips to facilitate gripping surrounding tissue when implanted.

Referring to FIG. 11, corresponding inflow and outflow surfaces of each of the fixation support structures 154, 156 can be covered with a web 168, 170 of flexible biocompatible material to provide respective inflow and outflow fixation support portions 173 and 175. The materials of each web 168, 170 can be the same as those mentioned in relation to the example of FIG. 2. For example, the web 168 can cover and be folded over the inflow end of the inflow support structure 154, such that the seam of the fold at the inflow end defines the inflow end 172 of the covered fixation support member 174. Similarly, the other end of the web 168 can cover and be folded over respective inflow and outflow ends of the inflow support structure 154, such that its seam at the opening 158 defines a contact end 176. The other support structure 156 can be covered by the web 170 in a similar manner, such that the web is folded over the ends to define an outflow end 178 of fixation support member and another contact end 180 thereof. Sutures or other means (e.g., adhesive, staples or the like) can be utilized for attaching the webs 168 and 170 to the respective support structure 154 and 156.

After each support structure 154, 156 has been covered with webs 168 and 170 to provide respective support portions 173 and 175, such as shown in FIG. 11, the respective contact ends 176 and 180 can be attached together and connected about the supported valve 16 to form the prosthesis 152. The inflow and outflow fixation support portions 173 and 175 thus form the corresponding fixation support member 174, such as shown in FIGS. 12 and 13.

By way of example, the respective contact ends 176 and 180 can be attached (e.g., by sutures) to the folded over portion of the web 84 at the inflow end 88 of the supported valve 16 similar to the example of FIGS. 3-5 shown and described herein. Additionally, prior to attachment to the supported valve 16, the respective inflow and outflow support portions 173 and 175 can be attached together at their contact ends 176 and 180 (e.g., anastomosis via sutures) which combined structure, defining the fixation support member 174, can then be attached at the inflow end 88 of the supported valve 16.

The fixation support member 174 of the prosthesis 152 can have a substantially V-shaped cross-sectional configuration of the 14 in its expanded cross-sectional dimension. In this example, however, the legs of the V-shaped cross section are formed of the opposing surfaces of the respective support structures 173 and 175. The space between the legs of the V-shaped cross-sectional configuration defines a receptacle, indicated at 184. The receptacle thus is dimensioned and configured for receiving tissue therein.

The angular relationship of the respective support structures 173 and 175 can also be implemented as discussed with respect to the example of FIG. 5. For instance, an angle between the facing surfaces of the respective inflow and outflow support portions 173 and 175 can be greater than 40°, typically ranging between 70 and 100°. Additionally, the angular contribution of the outflow portion 175 can be greater than that of the inflow portion, such as described with respect to FIG. 5, to better accommodate the dimensions and configurations of the mitral valve annulus, which may include the patient's native leaflets when the prosthesis 152 is implanted. Since according to one embodiment the prosthesis 152 can be implanted at the mitral position, the supported valve 16 can be provided with a diameter or size that is greater than 23 millimeters, such as ranging from about 25 millimeters to about 34 millimeters, or even larger. The prosthesis 174 thus can be configured to function and can be implanted as described with respect to FIGS. 8 and 9.

What has been described above includes examples of the present invention. It is, of course, not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, modifications and variations that fall within the scope of the appended claims.

What is claimed is:

1. A heart valve prosthesis comprising:
   a supported valve comprising a biological valve portion mounted within a support structure, the supported valve being configured to provide for substantially unidirectional flow of blood through the supported valve, the supported valve having inflow and outflow ends that are spaced axially apart from each other; and
   a fixation support member secured around an outer perimeter of the supported valve, the fixation support member comprising inflow and outflow portions, the inflow portion of the fixation support member extending from a radially inner contact surface of the fixation support member radially outwardly and axially in a direction of the inflow end of the supported valve upon deployment of the heart valve prosthesis, the outflow portion of the fixation support member extending from the radially inner contact surface radially outwardly and axially in a direction away from the inflow portion of the fixation support member upon deployment of the heart valve prosthesis, the radially inner contact surface being attached to a radially outer surface of the supported valve adjacent the inflow end of the supported valve, the supported valve and the fixation support member being deformable between a reduced cross-sectional dimension and an expanded cross-sectional dimension thereof when the heart valve prosthesis is deployed, whereby implantation of the heart valve prosthesis is facilitated,
   wherein the fixation support member comprises an annular support formed from a plurality of support features and having one of a U-shaped or V-shaped cross-sectional configuration for a longitudinal cross-section taken axially through the prosthesis in its expanded cross-sectional dimension, the support features alternate extending between the inflow and outflow directions along a circumferential path corresponding to the radially inner contact surface, the support features being interconnected at first junctures at an axial extent of the inflow portion and being interconnected at second junctures at an axial extent of the outflow portion, each support feature being directly connected to only two other support features such that the support features collectively extend along the entire axial length of the fixation support member.

2. The prosthesis of claim 1, wherein the fixation support member is flexible and deformable, the plurality of support features extending from the radially inner contact surface to terminate in respective distal ends thereof for biasing each of the inflow and outflow portions of the fixation support member toward the expanded cross-sectional dimension; and at least one web of flexible biocompatible material covering at least an inflow surface of the support features for the inflow portion and at least an outflow surface of the support features for the outflow portion.

3. The prosthesis of claim 2, wherein the flexible and deformable fixation support member comprises a continuous monolithic structure.

4. The prosthesis of claim 2, wherein at least some of the support features further comprise spikes that extend outwardly from respective support features toward the other of inflow or outflow portion of the fixation support member.

5. The prosthesis of claim 2, wherein the support structure of the supported valve further comprises a cylindrical support extending between the axially spaced apart inflow and outflow ends thereof, the cylindrical support of the support structure of the supported valve including a plurality of support features extending axially between the axially spaced apart inflow and outflow ends of the cylindrical support, adjacent pairs of the plurality of support features being interconnected so as to bias the cylindrical support radially outwardly toward the expanded cross-sectional dimension.

6. The prosthesis of claim 1, wherein a longitudinal cross-section axially through the prosthesis in its expanded cross-sectional dimension provides an angle between the inflow and outflow portions of the fixation support member that is greater than forty degrees, space between axially opposed surfaces of the inflow and outflow portions defines a receptacle around the outer perimeter of the supported valve that is dimensioned and configured for receiving therein tissue at a valve annulus.

7. The prosthesis of claim 6, wherein an angle of the inflow portion of the fixation support member relative to a plane extending transversely through the prosthesis at the radially inner contact surface of the fixation support member is less than an angle of the outflow portion of the fixation support member relative to the plane.

8. The prosthesis of claim 1, wherein the radially inner contact surface defines an apex and each of the inflow and outflow portions of the fixation support member define legs of a V-shaped cross-sectional configuration, a space between the legs of the V-shaped cross-sectional configuration defines a toroidal channel around the outer perimeter of the supported valve dimensioned and configured for receiving a heart valve annulus.

9. The prosthesis of claim 1, wherein the supported valve has an expanded cross-sectional dimension that is greater than 24 mm, the inflow and outflow portions of the fixation support member extending outwardly beyond the expanded cross-sectional dimension of the supported valve to provide an annular receptacle extending around the outer perimeter of the supported valve between the inflow and outflow portions of the fixation support member, the receptacle being dimensioned and configured for receiving tissue when implanted at a valve annulus.

10. The prosthesis of claim 1, wherein a valve portion of the supported valve comprises an animal tissue heart valve that is one of a homograft or xenograft.

11. The prosthesis of claim 10, wherein the animal tissue heart valve comprises a porcine heart valve.

12. The prosthesis of claim 1, wherein the support features of the inflow portion of the fixation support member comprise triangular support features and the support features of the outflow portion of the fixation support member comprise triangular support features, the triangular support features of the outflow portion connecting the triangular support features of the inflow portion together and spacing the triangular support features of the inflow portion apart from one another.

13. The prosthesis of claim 1, wherein the support features of the inflow portion are directly connected to one another in pairs, each directly connected pair of support features of the inflow portion being spaced from each other directly connected pair of support features of the inflow portion.

14. The prosthesis of claim 1, wherein the support features of the outflow portion are directly connected to one another in pairs, each directly connected pair of support features of the outflow portion being spaced from each other directly connected pair of support features of the inflow portion.

15. The prosthesis of claim 1, wherein the radially inner contact surface of the fixation support member is positioned around the outer perimeter of the support structure of the supported valve.

16. The prosthesis of claim 1, wherein the cross-section of the annular support of the fixation support member is V-shaped with a pointed apex.

17. A heart valve prosthesis comprising:
a supported valve comprising a biological valve portion mounted within a support structure, the supported valve being configured to provide for substantially unidirectional flow of blood through the supported valve, the supported valve having inflow and outflow ends that are spaced axially apart from each other and
a fixation support member secured around an outer perimeter of the supported valve, the fixation support member comprising inflow and outflow portions, the inflow portion of the fixation support member extending from a radially inner contact surface of the fixation support member radially outwardly and axially in a direction of the inflow end of the supported valve, the outflow portion of the fixation support member extending from the radially inner contact surface radially outwardly and axially in a direction away from the inflow portion of the fixation support member, the angle between the inflow and outflow portions of the fixation support member ranging between 70 degrees and 100 degrees
wherein the radially inner contact surface is attached to a radially outer surface of the supported valve adjacent the inflow end of the supported valve, the supported valve and the fixation support member being deformable between a reduced cross-sectional dimension and an expanded cross-sectional dimension thereof, whereby implantation of the heart valve prosthesis is facilitated,
wherein the fixation support member comprises an annular support formed from a plurality of support features and having one of a U-shaped or V-shaped cross-sectional configuration for a longitudinal cross-section taken axially through the prosthesis in its expanded cross-sectional dimension, the support features alternate extending between the inflow and outflow directions along a circumferential path corresponding to the radially inner contact surface, the support features being interconnected at first junctures at an axial extent of the inflow portion and being interconnected at second junctures at an axial extent of the outflow portion, each support feature being directly connected to only two other support features such that the support features collectively extend along the entire axial length of the fixation support member.

18. A heart valve prosthesis comprising:
a stented valve comprising a biological valve portion mounted within a stent, the stented valve being configured to provide for substantially unidirectional flow of blood through the stented valve, the stented valve having inflow and outflow ends that are spaced axially apart from each other; and a fixation support member extending around an outer perimeter of the supported valve, the fixation support member comprising inflow and outflow portions, the inflow portion of the fixation support member extending from a radially inner contact surface of the fixation support member radially outwardly and axially in a direction of the inflow end of the supported valve upon deployment of the heart valve prosthesis, the outflow portion of the fixation support member extending from the radially inner contact surface radially outwardly and axially in a direction away from the inflow portion of the fixation support member upon deployment of the heart valve prosthesis, a space between the inflow and outflow portions of the fixation support member defining a toroidal receptacle around the perimeter of the supported valve that is dimensioned and configured for receiving a heart valve annulus when the prosthesis is implanted at the heart valve annulus, wherein the fixation support member comprises a plurality of support features and having one of a U-shaped or V-shaped cross-sectional configuration for a longitudinal cross-section taken axially through the prosthesis in an expanded cross-sectional dimension thereof, the support features alternating extending between the inflow and outflow directions along a circumferential path corresponding to the radially inner contact surface, the support features being interconnected at first junctures at an axial extent of the inflow portion and being interconnected at second junctures at an axial extent of the outflow portion, each support feature being directly connected to only two other support features such that the support features collectively extend along the entire axial length of the fixation support member.

19. A heart valve prosthesis comprising:

a supported valve comprising a biological valve portion mounted within a support structure, the supported valve being configured to provide for substantially unidirectional flow of blood through the supported valve, the supported valve having inflow and outflow ends that are spaced axially apart from each other; and a fixation support member secured around an outer perimeter of the supported valve, the fixation support member comprising inflow and outflow portions, the inflow portion of the fixation support member extending from a radially inner contact surface of the fixation support member radially outwardly and axially in a direction of the inflow end of the supported valve, the outflow portion of the fixation support member extending from the radially inner contact surface radially outwardly and axially in a direction away from the inflow portion of the fixation support member, the inflow portion and outflow portion of the fixation support member having essentially the same length from the radially inner contact surface, wherein the radially inner contact surface is attached to a radially outer surface of the supported valve adjacent the inflow end of the supported valve, the supported valve and the fixation support member being deformable between a reduced cross-sectional dimension and an expanded cross-sectional dimension thereof, whereby implantation of the heart valve prosthesis is facilitated, wherein the fixation support member comprises an annular support formed from a plurality of support features and having one of a U-shaped or V-shaped cross-sectional configuration for a longitudinal cross-section taken axially through the prosthesis in its expanded cross-sectional dimension, the support features alternate extending between the inflow and outflow directions along a circumferential path corresponding to the radially inner contact surface, the support features being interconnected at first junctures at an axial extent of the inflow portion and being interconnected at second junctures at an axial extent of the outflow portion, each support feature being directly connected to only two other support features such that the support features collectively extend along the entire axial length of the fixation support member.

\* \* \* \* \*